United States Patent [19]

Sauder

[11] 4,026,299

[45] May 31, 1977

[54] COOLING AND HEATING APPARATUS

[75] Inventor: James W. Sauder, San Ysidro, Calif.

[73] Assignee: Vari-Temp Manufacturing Co., El Cajon, Calif.

[22] Filed: Sept. 26, 1975

[21] Appl. No.: 616,909

[52] U.S. Cl. ............................................. 128/400
[51] Int. Cl.² ......................................... A61F 7/00
[58] Field of Search .......... 128/400, 399, 402, 379, 128/380

[56] References Cited

UNITED STATES PATENTS

| 1,896,953 | 2/1933 | Hassell | 128/400 X |
| 2,110,022 | 3/1938 | Kliesrath | 128/400 |
| 2,260,134 | 10/1941 | Ballman | 128/400 |
| 2,415,455 | 2/1947 | Barnes et al. | 128/400 |
| 2,726,658 | 12/1955 | Chessey | 128/400 |
| 3,918,458 | 11/1975 | Nethery | 128/400 |

Primary Examiner—Lawrence W. Trapp
Attorney, Agent, or Firm—Jerry R. Seiler

[57] ABSTRACT

An improved portable apparatus for selectively heating and cooling a body portion comprises a unit having at least one flexible pad and tubing for being wrapped around a body portion and acting as an evaporator on cooling and a condenser on heating, a compressor, a condenser acting as an evaporator on heating, a fan for moving air through the condenser, conduits for directing refrigerant composition in the unit, valve means for selectively reversing the flow of refrigerant to alternately cool and heat the pad and tubing, and a carrying case for the apparatus having a lid, bottom, front, back and side panels cooperating to form a chamber in which the apparatus is received, and a port in both the front and back panels for directing air into and from the chamber when the fan is operating. Other embodiments of the apparatus also include quick-connect couplings between the apparatus and pad refrigerant conduits, an auxiliary heat exchanger and heater, means for recharging the refrigerant composition in the apparatus, and novel flexible pads, especially useful for wrapping around human or animal body portions for cooling or heating thereof.

16 Claims, 4 Drawing Figures

COOLING AND HEATING APPARATUS

BACKGROUND OF THE INVENTION

In patent application Ser. No. 422,758, filed Dec. 7, 1973 and now U.S. Pat. No. 3,916,911, there is disclosed a portable heating and cooling apparatus utilizing flexible pads to be wrapped around a limb or other body portion of a human or animal, for selectively heating or cooling that body portion. The portable apparatus is especially useful in treating sprains, strains or other muscular injuries to athletes or race horses, as soon after the injury occurs as possible in order to rapidly reduce swelling, fever or the like to the injured area. Such a device obviates the inconvenient use of ice packs for treating such injuries or muscular diseases or inflamations. The present invention is an improvement over the previous apparatus. The unit is combined with a carrying case having special features of quick connect and disconnect means, and refrigerant recharge means. Especially important are an auxiliary heat exchanger and improved flexible pad design as will be more fully explained hereinafter.

SUMMARY OF THE INVENTION

The present invention provides an improved portable heating and cooling apparatus which can be readily transported utilizing a carrying case of particular design. The heating and cooling unit is enclosed in the carrying case cavity which case is provided with ports through which ambient air is drawn for cooling the condenser when the apparatus is in a cooling cycle or bringing the warmer ambient air over the evaporator coils during a heating cycle. Quick connect and disconnect means in the form of fluid line couplings are used for easily and rapidly removing and connecting interchangeable flexible pads.

In another embodiment, the device incorporates a one way valve conveniently located for recharging refrigerant in the apparatus using a can of pressurized refrigerant. In yet another embodiment, there are provided improved flexible pads utilizing flexible tubing removably secured on one side of an insulating material with a non-insulating sheet removably secured to the insulating material and covering the tubing, with the pad wrapped around a limb or body portion, heat or cold is readily transferred through the inner non-insulating cover while loss of heat or cold is minimized because of the heat insulating cover. In still another embodiment an auxiliary heat exchanger, acting as an auxiliary evaporator or accumulator during cold cycle use of the apparatus and used in combination with a resistance heating element to create an artificial ambient temperature during heating cycles of the apparatus improves cold and hot temperatures respectively at the pad. Specific characteristics and uses of the apparatus and the various embodiments will be more evident from the following detailed description.

DETAILED DESCRIPTION OF THE INVENTION

Figure 1:
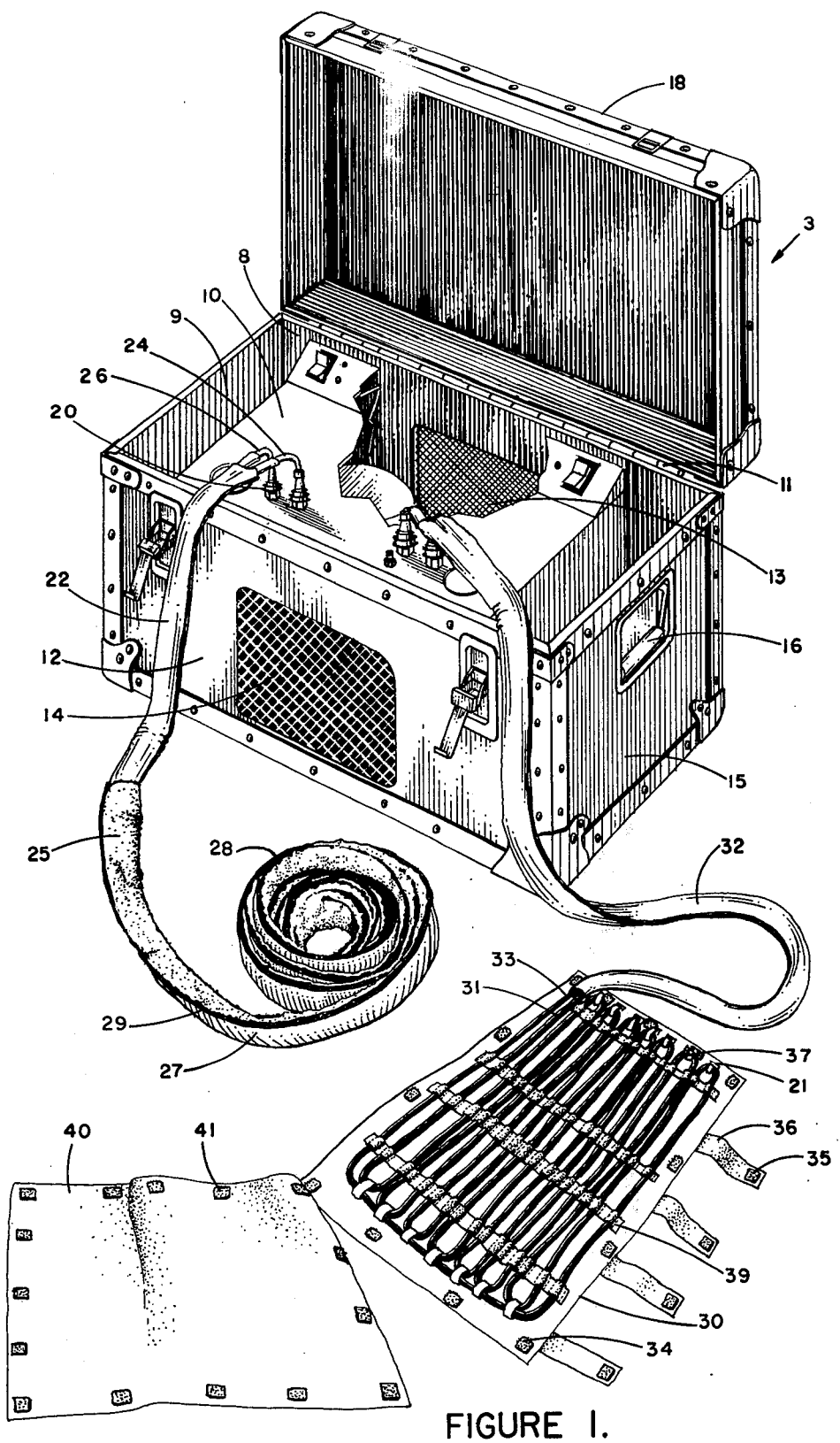
FIG. 1 is a perspective view illustrating the portable carrying case for the apparatus, and flexible heating pads, one of which is opened to show the arrangement of the components.

Referring first to FIG. 1, there is illustrated the heating and cooling unit in phantom 10 of the invention disposed in a carrying case 3. The carrying case has front and back panels 12 and 8 respectively, side panels 9 and 15, a bottom (not seen) and a lid 18. These components define a chamber or cavity in which the heating and cooling unit 10 is placed, including a compressor, condenser, fan for moving air through the condenser, conduits for directing refrigerant opposition in the unit, a reversing valve for reversing the flow of refrigerant through the components, capillary tubes, and an auxiliary heat exchanger and resistance heating element. These components are thus easily transported by a person utilizing handles 16, and are also protected from damage during use and transportation. A necessary feature of the carrying case as it is adopted particularly for the present invention are a pair of ports 13 and 14 in the back and front panels, respectively. port 13 is shown through the cover of the unit. The unit is situated in the carrying case with the condenser disposed adjacent back port 13 so that a power driven fan for cooling the condenser (in a cold cycle) will draw air through front port 14, past the fan, and through the condenser with the hot air from the coils discharged through port 13. Without such ports, the efficiency of the unit would be significantly altered.

The carrying case may include hinges 11 attached to back panel 8 and lid 18 so that the lid may be raised or lowered. Other features including latches for the lid in the closed position and the like may be used as will be evident to those skilled in the art. Again, the use of such a carrying case significantly increases the portability of the apparatus as well as protecting the components during storage and use. The case may comprise any suitable material including impact resistant plastics, aluminum, fiberglas and the like with the lightweight and high impact materials being especially preferred. A screen material may also be used to cover the front and back ports in order to prevent foreign objects from entering the unit which could cause damage to the components.

FIG. 1 also illustrates novel flexible pads particularly useful in treating human body portions, for heating or cooling. The open pad shown has an outside flexible insulating sheet 30, preferably of a rubber composition and having a fabric back layer, such as material commonly being used for wet suits and the like. Such a rubbery composition provides excellent heat insulation and at the same time is reasonably lightweight and easy to form to any desired shape around a limb or other body portion. Secured to the inside surface sheet 30 is a flexible hose or tubing, comprising joined tubing 31 and 33 for directing refrigerant composition to and from the pad and which tubing is removably secured in a plurality of straps 37. Conveniently, one end of strap 37 may be secured to the insulating sheet and the other end releasably secured with a buckle, snap or the like. Preferably, the strap end may be fastened with Velcro, a material in which one mating surface has a plurality of fabric loops while the opposite surface comprises small, flexible barbs or hooks for engaging the loops described, for example, in U.S. Pat. No. 3,461,511 or 3,387,345. Regardless of the type of disengagable devices used for securing the end of strap 37, a plurality of straps are located at selected positions on the interior surface of insulated sheet 30 by which the flexible refrigerant directing conduit or tubing is secured to the sheet. Spaced around the periphery of the inside surface or interior of the insulated sheet are Velcro portions 34 for engaging opposite Velcro portions 41 on non-insulating inner sheet 40. Again, it will be understood that patches 34 comprise loops, the opposite portions 41 will comprise the hooks. Thus, non-insulating inner sheet 40 can be readily secured to insulating exterior sheet 30 by simply pressing the fastening means of the respective sheets against one another whereby sheet 40 covers the flexible tubing loops.

It will be understood that other equivalent means for securing the sheets together such as snaps, zippers, and the like may be used so long as they can be disengaged for removing the inner sheet. The purpose for this feature is so that the non-insulating sheet, which will be applied or lie against the patient's limb during use of the apparatus, may become soiled or worn, and thus can be removed, washed or otherwise cleaned for sanitary purposes, or replaced. Further, removal or disengagement of this non-insulating inner sheet exposes the tubing for repairs or replacement. A tape 39 may be used for securing the plurality of tubing loops together so that the desired tubing shape will be retained. Preferably, the tape is also removable so that the tubing may be formed into different shapes, such as shown with pad 28. Also included are a plurality of straps 36 also having Velcro patches 35 or equivalent means for holding the pad in a wrapped position around a limb during use. The size of the pad including outer sheet 30 and inner sheet 40 is such that it can be wrapped around a limb to substantially entirely enclose it with straps 36 holding the pad in place.

Flexible pad 28 is elongated and relatively narrow, also having an insulating outside sheet 27 and a non-insulating and detachable inside sheet 25, separated along seam 29. These inside and outside sheets are the same as those of the previously described pad except for their shape. Thus, exterior sheet 27 is formed of a thermal insulating material and having means along the inside surface for detachably securing non-insulating sheet 25. Between the two sheets are a pair of flexible joined tubes for delivering refrigerant composition to and from the pad. Such an elongated and narrow flexible pad may be wrapped around a patient's abdomen, back and chest, shoulder and the like, unlike the previously described pad of the more conventional square or rectangular shape. The length of such a pad is not so critical but for the stated wrapping use should be at least about 5 feet in length, and having a width of between about 3 and about 6 inches to accommodate the unlooped pair of tubes.

Figure 2:
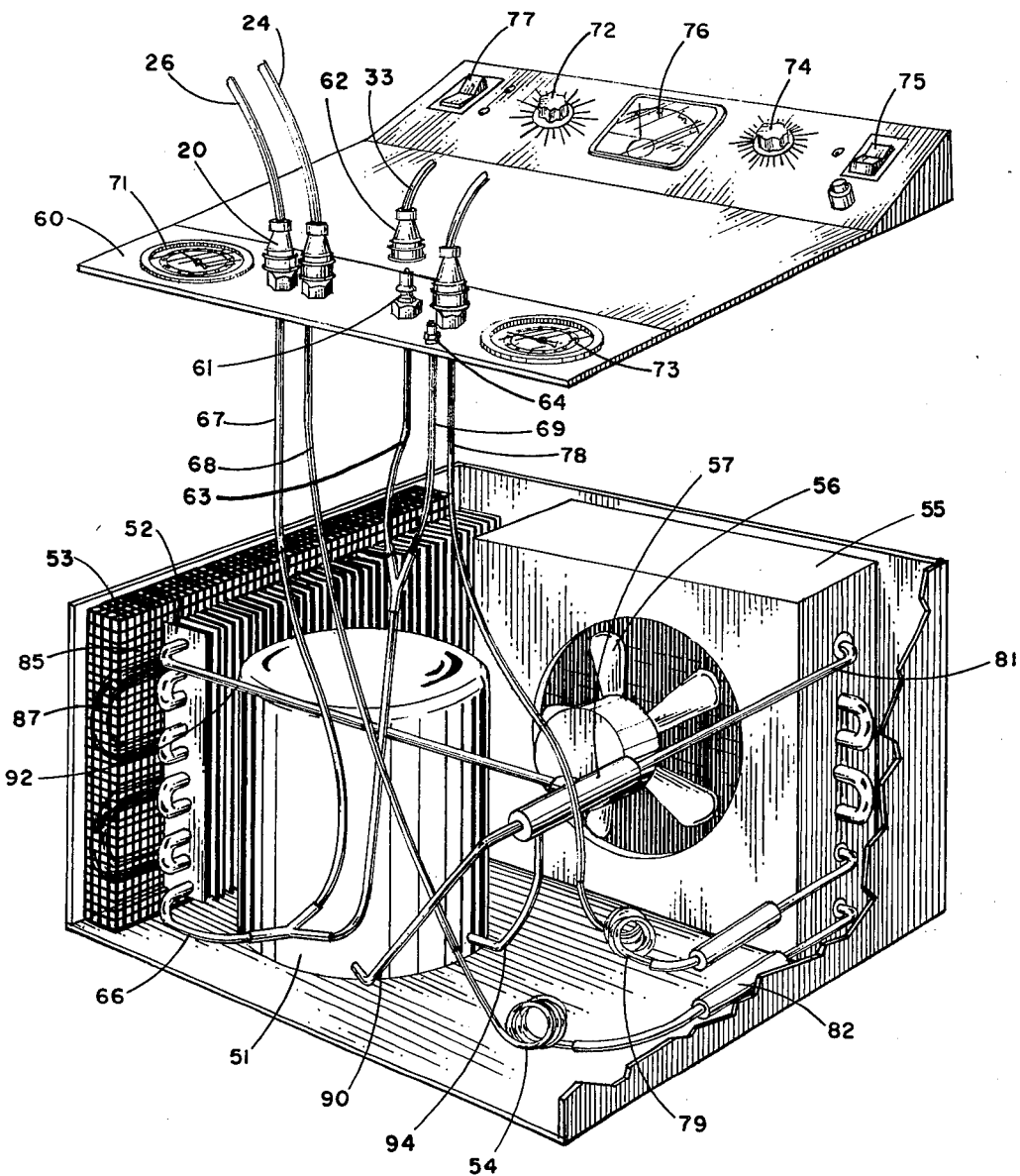
FIG. 2 is a perspective illustration of the heating and cooling unit out of the case, partially exploded and broken away.

It is to be understood that the flexible tubing 31 and 33 through which refrigerant passes to the pads also extend to the unit itself or are otherwise connected to flexible conduits between the pads and the unit. For example, as shown in FIG. 2, flexible refrigerant directing conduits 24 and 26 are secured to connecting members 20 located on top plate 60 of the unit. Moreover, in order to reduce thermal losses between the unit and the pads, it is desirable to enclose or wrap the otherwise exposed conduits or tubes with an insulating material such as insulating covers 22 and 32 shown in FIG. 1. The covers may be any suitable thermal insulating material such as that used for the back or exterior pad sheet previously described.

Figure 3:
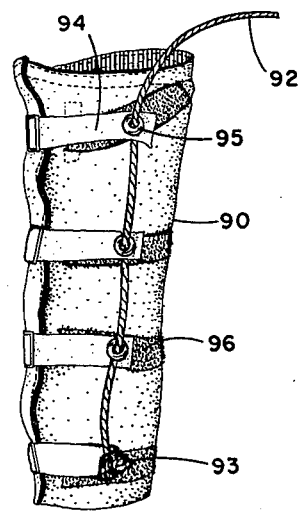
FIG. 3 is a side view of another flexible pad embodiment, especially useful for a horse leg.

Referring to FIG. 3, there is illustrated another pad, particularly suited for being wrapped around the limb of a horse or other animal which is to be treated utilizing the apparatus of the invention. The pad has an exterior cover sheet 90, also preferably being a thermal insulating material as previously described and with a detachably secured non-insulating sheet. Flexible heating tubes will be secured between these interior and exterior sheets, also in a manner previously described regarding pad 30 in FIG. 1. The advantage of the flexible pad illustrated is the use of a safety means in the form of a cord 92 which passes through eyelets 95 on closure straps 94. The closure straps have snap, Velcro or other securing means along their inner surface cooperating with patches 96 for maintaining the straps in a closed position when the pad is placed around the animal's limb. Cord 92 passes through an eyelet 95 on each of the straps and is secured to the lower strap by a knot 93 or similar means at the cord end. The use of such a safety feature requires that cord 92 be secured to a stationary structure, for example, by tying it to a portion of a stall or fence where the animal is being treated. The length of the cord extending between the structure and the animal must be shorter than the tubing length between the unit and the animal. Thus, the animal moves to a distance from the unit which is further than the length of the refrigerant directing flexible hoses, cord 92 will pull open the straps thereby releasing them and opening the pad. The open pad will fall away of its own weight rather than pulling on the tubing which could rupture, cause loss of refrigerant, or other damage to the apparatus.

FIG. 2 illustrates the apparatus or unit, that shown being selectively for heating and cooling and incorporating a reversing value 57 for reversing the direction of the refrigerant flow. However, it should be appreciated that in the embodiments described herein, the apparatus may be used only for cooling, rather than the heating and cooling device of the preferred embodiment. The apparatus shown includes a cover plate 60 on which are located various controls, switches and gauges which are of assistance in utilizing the apparatus. Specifically, these controls include a reversing switch 77, cooperating with suitable electrical switches and solenoids for energizing and operating reversing valve 57 which valve will designate the direction in which the refrigerant composition is passing through the conduits and other components of the apparatus. Also included are an off/on switch 75 for directing power to operate the unit, a temperature control selector 72 for thermostatically selecting the time for which the unit will operate and which timer is electrically connected to the power or on/off switch for shutting the unit down after a desired amount of time. Such controls are for convenience and enhance the ease in which the apparatus is utilized or operated. In addition, high and low pressure gauges 71 and 73, also optional, will indicate the refrigerant pressure in the apparatus so that where pressure is low, additional refrigerant may be added or charged to the system, and where too high, some refrigerant may be bled off.

It has been found advantageous to incorporate quick-connect couplings 20 which comprise a socket member 62 attached to the end of flexible conduit 33 and plug 61 secured to cover plate 60 and to which conduit 63 is attached. These quick-connect couplings are shut off couplings, of the type referred in U.S. Pat. 2,823,048 and allow for easy connection or disconnection between the socket and plug portions without loss of refrigerant in the system. Accordingly, using such couplings, one type of pad may be quickly disconnected and another substituted therefor. Again, for use in the apparatus, the plug portion of the coupling is secured to top plate 60 as are the internal conduits of the apparatus in a manner illustrated in FIG. 2.

Another feature of the apparatus of the invention comprises the use of means for recharging or replenishing refrigerant composition. It has been found that the flexible rubber or reinforced elastomer or rubber tubing used for the pad is somewhat porous as compared to metal tubing such as copper. Thus, there is some permeation of the refrigerant through the tubing. This is found to be especially a problem when the apparatus is used on the heating cycle, i.e., where the pad acts as condensers thereby giving off heat, since heating of the rubber tubing causes it to expand somewhat thereby increasing permeation of refrigerant through the molecular size pores of the tubing composition. With such usually slow but eventual loss of some of the refrigerant, it is desirable to be able to easily replenish the refrigerant so that the apparatus functions at optimum efficiency. Again, loss of the refrigerant can be detected, especially in the preferred embodiment where the pressure gauges 71 and 73 are utilized. For a convenient replenishing means, a one way valve 64 is secured to cover plate 60 and which valve is connected to the refrigerant system via conduit 69. Valve 64 may be provided with a cap which may be removed and a cannister or bottle of pressurized refrigerant having a hose and means for opening the valve may be connected thereto and a suitable or desirable amount of refrigerant forced into the apparatus. Valve 64 should be of the type that automatically closes when the opening means is removed as will be understood by those skilled in the art.

Figure 4:
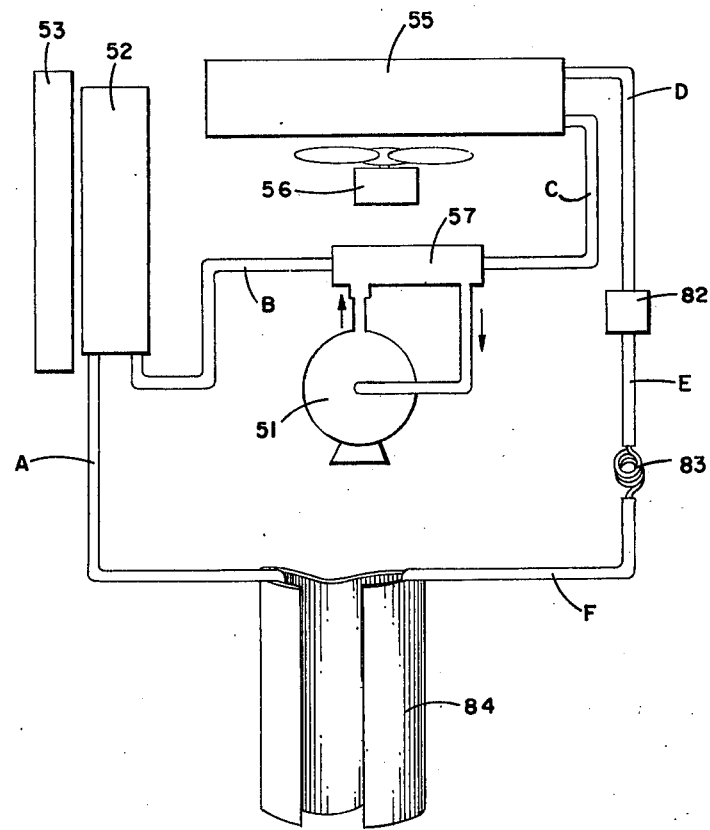
FIG. 4 is a schematic view illustrating the components of the apparatus of the invention and their relationship in refrigerant flow.

Other components of the apparatus shown in FIG. 2 include compressor 51, condenser 55, which also acts as an evaporator during the heating cycle, motor driven fan 56 for passing ambient air over coils of condenser 55, conduits 66, 67, 68, 69, 78, 81, 90, 92 and 94 for directing refrigerant composition through the system and to the flexible exterior conduits or hoses to the pads, driers 82, and capillary tubes 54 and 79. In another preferred embodiment, there is utilized an auxiliary heat exchanger 52. A heater 53, having grills 85 and a resistance heating element 87 is located adjacent to the auxiliary heat exchanger. The purpose of the auxiliary heat exchanger is to act as an auxiliary evaporator on the cold cycle and an auxiliary condenser on a heating cycle. This may be explained by observing FIG. 4 which shows relationships of the pad 84, condenser 55, compressor 51, reversing valve 57, auxiliary heat exchanger 52 and heater 53. For example, during a cooling cycle, pad 84 acts as an evaporator thereby being cooled as liquid refrigerant passing into the pad tubing is evaporated to a gaseous state by absorbing heat. In an apparatus of this type functioning without an auxiliary heat exchanger 52, the gas refrigerant from pad 84 would pass through the reversing valve 57 and into compressor 51. However, if incomplete evaporation allowed some liquid refrigerant along the bottom of the conduits to be directed into the compressor, it would cause damage or at least malfunctioning. Thus, observing particularly FIG. 4, in the cold cycle of the apparatus, cold pad 84, acting as an evaporator evaporates liquid refrigerant which is directed first through conduit A to bottom side of auxiliary heat exchanger 52 where there takes place further evaporation of the refrigerant in its elongated coils. Heat exchanging fins attached to the coils are at a higher temperature than the refrigerant passing through the heat exchanger thus further elevating the refrigerant temperature. Gaseous refrigerant composition then passes from the top side of the auxiliary heat exchanger via conduit B to reversing valve 57 and, following the arrows, into the suction side of compressor 51 where it is compressed and driven out of the high compressor side, back through the reversing valve, conduit C and to the top side of condenser 55. In the condenser, the refrigerant is condensed in the tubes which are also in direct contact with heat exchanging fins and over which fins and tubes ambient air is driven by fan 56. The refrigerant, losing heat, becomes liquified and is drawn from the bottom side of the condenser, via conduit D through drier 82, conduit E, capillary tube 83, conduit F and into cooling pad 84, acting as an evaporator and so on. Thus, in this cooling phase the auxiliary heat exchanger 52 acts to further evaporate any remaining liquid refrigerant not been completely evaporated in pad 84 to further improve the efficiency of the system as well as to prevent malfunction.

In the heating cycle, pad 84 acts as a condenser whereby gaseous refrigerant passing thereto via conduit A becomes condensed to a liquid as the pad 84 gives off heat. Liquid refrigerant then passes via conduit F through capillary tube 83, conduit E, drier 82, conduit D, and into the bottom side of evaporator 55. It will be understood that evaporator 55 in this instance is of larger capacity than auxiliary heat exchanger 52, having greater coil and heat exchange surface as well as having ambient air driven thereover by fan 56. Gaseous refrigerant then passes from the top evaporator side, via conduit C through reversing valve 57, compressor 51, reversing valve, conduit B and into the top side of auxiliary heat exchanger 52. In this hot cycle or heating phase of the apparatus, resistance heater 53 is electrically connected to reversing valve 57 or otherwise energized by hot-cold switch 77 shown in FIG. 2 so that it transfers heat to auxiliary heat exchanger 52. This will further increase the temperature of the gaseous refrigerant composition which then passes from the bottom side of the auxiliary heat exchanger via conduit A into heating pad (condenser) 84. Thus, in this heating cycle, the auxiliary head exchanger in combination with the heater 53 elevates the temperature of the refrigerant composition to further increase the heating temprature of the pad, thereby increasing the efficiency and effectiveness of the apparatus.

The apparatus described herein including its various embodiments is a significant improvement in achieving greater efficiency and effectiveness of the intended system, both in the heating and cooling cycles, as well as providing improved flexible pad characteristics and other features to enhance the ease in which the system is utilized. These as well as other advantages of the preferred embodiments of the apparatus herein described as well as modifications thereof within the purview of the invention, will be evident to those skilled in the art.

I claim:

1. A portable apparatus for cooling a body portion comprising a cooling unit having an evaporator pad and tubing for being wrapped around said body portion and in which vaporized refrigerant composition cools said pad, a compressor and a condenser for liquefying refrigerant composition, a fan for moving air for cooling said condenser, an auxiliary evaporator, conduits for directing refrigerant composition in said unit and to and from said pad and tubing for cooling thereof, and a carrying case for said unit comprising a lid, a bottom, front, back and side panels cooperating to form a chamber in which said unit is received, wherein said front and back panels each have a port therein for directing air into and from said chamber when said fan is operating.

2. The apparatus of claim 1 wherein said condenser is disposed adjacent one of said ports.

3. The apparatus of claim 1 including a pair of elongated flexible hoses extending between said pad and said unit, and a quick-connect coupling between each one of said hoses and said unit said coupling comprising a socket on the end of said flexible hose and a plug on said unit.

4. Apparatus of claim 3 including a top plate covering said compressor, condenser, fan and conduits, wherein said plugs are secured on said plate.

5. Apparatus of claim 4 including one-way valve means secured on said plate for replenishing said unit with refrigerant composition.

6. A portable apparatus for selectively heating and cooling a body portion comprising a unit having at least one flexible pad and tubing for wrapping around said body portion acting as an evaporator on cooling and a condenser on heating, a compressor, a condenser acting as an evaporator on heating, a fan for moving air through said condenser, conduits for directing refrigerant composition in said unit, and valve means for selectively reversing the flow of refrigerant to alternately heat and cool said pad and tubing, and a carrying case for said unit comprising a lid, a bottom, front, back and side panels cooperating to form a chamber in which said unit is received, wherein said front and back panels each have a port therein for directing air into and from said chamber when said fan is operating.

7. The apparatus of claim 6 wherein said condenser is disposed adjacent one of said ports.

8. Apparatus of claim 6 including a pair of elongated flexible hoses extending between said pad and said unit, and a quick connect coupling between each one of said hoses and said unit said coupling comprising a socket on the end of said flexible hose and a plug on the end of said conduit.

9. Apparatus of claim 8 including a top plate covering said compressor, condenser, fan and conduits, wherein said plugs are secured on said plate.

10. Apparatus of claim 9 including one-way valve means secured on said plate for replenishing said unit with refrigerant composition.

11. In a portable apparatus for selectively heating and cooling a body portion comprising a heat pump having at least one flexible pad and tubing for wrapping around said body portion acting as an evaporator on cooling and a condenser on heating, a compressor, a condenser acting as an evaporator on heating, a fan for moving air through said condenser, conduits for directing refrigerant composition in said unit, and valve means for selectively reversing the flow of refrigerant to alternately heat and cool said pad and tubing, the improvement comprising an auxiliary heat exchanger through which refrigerant is passed from said compressor during heating and from said pad during cooling.

12. The apparatus of claim 11 including a resistance heater adjacent said auxiliary heat exchanger through which heater current is passed during said heating thereby heating said heat exchanger.

13. In a pad for supplying heat or cold to a body portion, the improvement comprising a flexible thermal insulating sheet, a length of flexible hose removably non-insulating to one side of said insulating sheet and a non-insulatig sheet detachably secured to said insulating sheet and covering said flexible hose.

14. The pad of claim 13 including means for releasably holding said pad in a wrapped position around said body portion.

15. The pad of claim 14 including safety means for releasing said holding means when said pad is moved a predetermined distance.

16. The pad of claim 15 wherein said safety means comprises a cord attached to said holding means and secured to a stationary structure whereby movement of said pad beyond the length of cord extending between said structure and said pad will cause said holding means to be released and said pad opened.

* * * * *